(12) United States Patent
Stemmler et al.

(10) Patent No.: US 7,011,955 B1
(45) Date of Patent: Mar. 14, 2006

(54) QUANTITATIVE DETERMINATION OF ANALYTES IN A HETEROGENEOUS SYSTEM

(75) Inventors: Ivo Stemmler, Tuebingen (DE); Andreas Brecht, Waldbronn (DE); Gunter Gauglitz, Tuebingen (DE); Michael Steinwand, Owingen (DE)

(73) Assignee: Universitaet Tuebingen, Tuebingen (DE)

( * ) Notice: Subject to any disclaimer, the term of this patent is extended or adjusted under 35 U.S.C. 154(b) by 0 days.

(21) Appl. No.: 09/492,214

(22) Filed: Jan. 27, 2000

(30) Foreign Application Priority Data

Jan. 29, 1999  (DE) ............................... 199 03 576

(51) Int. Cl.
*G01N 33/543* (2006.01)
*G01N 33/547* (2006.01)

(52) U.S. Cl. ................... 435/7.93; 435/7.1; 435/7.8; 435/7.92; 435/7.94; 435/287.2; 435/287.9; 435/288.3; 435/288.4; 436/501; 436/512; 436/514; 436/517; 436/518; 436/525; 436/537; 436/538; 436/540; 436/66; 436/164; 436/165; 422/58; 422/68.1; 422/82.05

(58) Field of Classification Search ................ 435/2, 435/4, 5, 6, 7.1, 7.4, 7.8, 7.92, 7.93, 7.94, 435/19, 21, 23, 41, 24, 262, 287, 288, 291, 435/283.1, 289.1, 304.1, 310–312, 287.2, 435/287.9, 288.3, 288.4; 436/501, 504, 514, 436/518, 517, 525–542, 66, 172, 810, 824, 436/512, 164, 165, 809; 422/58, 62, 68.1, 422/82.05
See application file for complete search history.

(56) References Cited

U.S. PATENT DOCUMENTS

| | | | |
|---|---|---|---|
| 4,318,707 A | 3/1982 | Litman et al. | |
| 4,680,275 A | 7/1987 | Wagner et al. | |
| 4,748,129 A | 5/1988 | Chang et al. | |
| 4,977,077 A | 12/1990 | Ngo et al. | |
| 5,232,830 A | 8/1993 | Van Ness | |
| 5,283,339 A * | 2/1994 | Arnold et al. | 548/104 |
| 5,296,347 A * | 3/1994 | LaMotte, III | 435/5 |
| 5,381,224 A | 1/1995 | Dixon et al. | 356/72 |
| 5,510,247 A * | 4/1996 | Komives et al. | 435/41 |
| 5,514,592 A * | 5/1996 | Schoener et al. | 436/66 |

(Continued)

FOREIGN PATENT DOCUMENTS

CA   2 123 801   5/1993

(Continued)

OTHER PUBLICATIONS

Piehler et al., Assesment of affinity constants by rapid solid phase detection of equilibrium binding in a flow system, J. Immunol. Methods 201(2): 189-206 (1997).*

(Continued)

*Primary Examiner*—Long V. Le
*Assistant Examiner*—Gailene R. Gabel
(74) *Attorney, Agent, or Firm*—Kalow & Springut LLP

(57) ABSTRACT

The invention concerns a method for quantitative or qualitative determination of an analyte or its interaction or reaction kinetics in a system with at least two different phases, comprising the step of taking at least one measurement signal from at least one of the phases, whereby the different phases are present in parallel when taking the signal and whereby each measurement signal is attributed to one of at least two phases. In addition, the invention concerns a sample carrier, in particular for use in the method constituting the invention with one or more wells. The sample carrier is characterized by the fact that at least a portion of the sample carrier at least in the range of one or more wells is coated with fluorescence-quenching material.

41 Claims, 5 Drawing Sheets

Distribution of Intensity

Distribution of Fluorophores

U.S. PATENT DOCUMENTS

| | | | |
|---|---|---|---|
| 5,514,785 A | | 5/1996 | Van Ness et al. |
| 5,667,976 A | | 9/1997 | Van Ness et al. |
| 5,674,699 A | * | 10/1997 | Saunders et al. .......... 135/7.93 |
| 5,700,646 A | | 12/1997 | Wood |
| 6,121,055 A | * | 9/2000 | Hargreaves ................. 436/526 |
| 6,127,139 A | * | 10/2000 | Te Koppele et al. .......... 435/24 |
| 6,136,960 A | * | 10/2000 | Chait et al. ................. 530/412 |
| 6,312,906 B1 | | 11/2001 | Cass et al. |
| 6,361,944 B1 | * | 3/2002 | Mirkin et al. ................... 435/6 |
| 6,667,179 B1 | * | 12/2003 | Selvin ........................ 436/517 |

FOREIGN PATENT DOCUMENTS

| | | |
|---|---|---|
| CA | 2 291 621 | 12/1998 |
| EP | 0 671 622 | 9/1995 |
| EP | 0 779 254 A1 | 6/1997 |
| JP | 62-66141 A2 | 3/1987 |
| WO | WO94/16313 | 7/1994 |
| WO | WO 94/21379 A WO | 9/1994 |
| WO | WO 88/07202 | 9/1998 |

OTHER PUBLICATIONS

Lutz et al., Implementation of affinity solid phases in continuous flow biochemical detection, Journal of Chromatography A 776(2): 169-178 (1997).*

Hellen, H. et al. "Fluorescence emission at dielectric and metal-film interfaces" Optical Society of America (Optical Physics), vol. 4, No. 3, Mar. 1987, pp. 337-350.

Blair, S., et al. "Resonant-enchanced evanescent-wave fluorescence biosensing with Cylindrical optical cavities", Applied Optics, Optical Society of Americaa, Washington, US, vol. 40, No. 4 Feb. 1, 2001, pp. 570-582.

International Search Report for EP 00 10 1102.

International Search Report for EP 00 10 1102 (Sep. 2004).

* cited by examiner

QUANTITATIVE DETERMINATION OF ANALYTES IN A HETEROGENEOUS SYSTEM

FIELD OF THE INVENTION

The present invention relates to a method for quantitative determination of an analyte in a system comprising at least two different phases. Additionally, the present invention relates to a test sample carrier that is particularly suited to carrying out the method which constitutes the invention.

BACKGROUND OF THE INVENTION

The prior art describes numerous methods for quantitative determination of an analyte in a specified analysis sample. The various detection reactions are based on different principles. These include conversion of the analyte to be detected to a demonstrable substance, in which case, for instance, a coloured compound is produced and the degree of colouration is a measurement of the quantity of the analyte in question. Other detection methods are based on specific interactions between the analyte and a bonding partner. These include, for example, the detection method utilising the specific interaction between an antigen and an antibody, a ligand and its associated receptor or the hybridisation of complementary nucleic acid molecules. This type of detection method or assays are generally also described as affinity assays. With the affinity reactions on which they are based, there is generally the production of a stoichiometrically defined but not covalent complex formed from bonding partners specific to the analyte (e.g. a receptor, antibody) and the analyte (e.g. a ligand, antigen). Frequently, biomolecules like proteins take part in these reactions. But reactions can also exist between low-molecular substances, e.g. low-molecular receptor ligands, and a high-molecular substance, e.g. the receptor. A special variation of this affinity assay is based on immuno-assay in which the specific interaction between an antibody and an antigen is exploited. At the level of nucleic acid, a specific interaction can take place between two different nucleic acid molecules by means of mutually complementary sequential segments. By means of hybridisation of the complementary sequences, the formation of a double-stringed nucleic acid molecule results.

The assays cited are applied in numerous technical fields. These include clinical analysis/diagnostics, environmental analysis, genome analysis, active ingredient testing and even gene expression studies and gene bank screenings. Frequently several hundred samples are tested in parallel on a single sample carrier. This so-called "micro-array technique" nowadays achieves increased significance in so-called "high-throughput screenings".

The advantage with assays based on affinity reactions when compared with assays based on chemical conversion of the analyte is that more elaborate preparation of the sample is generally not required. Separation of the analyte from undesirable impurities is rather accomplished by means of the specific interaction with a suitable bonding partner, the latter deliberately selecting, as it were, the analyte desired from the analysis sample.

Immuno-assays constitute a particularly widespread variant of affinity assays based on the specific interaction of antibodies and antigens. In the case of so-called ELISA (Enzyme Linked Immuno-Sorbent Assay), one of the reactants (i.e. either the analyte or the associate bonding partner) is in the sample carrier, frequently constituting a micro-titre plate, in immobilised form. In the course of the test, one or more components of the test system form a complex with the immobilised component. The quantity of the complex formed serves as a measurement of the concentration of the analyte in the sample. Two common variants of this test format are made up of the "sandwich assay" and the "competitive assay". With the sandwich assay, for instance, the analyte is complexed by two further components (often two different antibodies) so that a ternary complex is generated on the sample carrier's surface. With the competitive assays, the analyte and a labelled component, frequently an analyte carrying a marker, compete f or a limited number of bonding positions.

A standard immuno-assay in heterogeneous phase frequently comprises the following processes:
Specification of a solid sample carrier;
Administration of analysis sample and a detection reagent;
Waiting for the binding equilibrium to set;
Rinsing out unbonded segments;
Measuring the bonded segments.

Where applicable, these steps can be repeated several times with complex protocols. At the end of the entire process, detection of the entire material then occurs which has been bound to the sample carrier in the course of the procedure. For this, a colouring enzyme reaction, electrochemical luminescence, fluorescence, radioactivity, etc. can be used as a signalling transmitter.

Some assay formats work in homogeneous phase, such as, for instance, the FPIA fluorescence polarisation immuno-assay, but which are in many respects complex or less flexible in the way of modification than assays in heterogeneous phase.

Common to practically all assays cited is that prior to the measurement signal separation of unbonded label (activity, measurement signal) and bonded label must take place. This is generally achieved by having the sample carrier subjected to one or more washing actions prior to measurement (taking the measurement signal). These washing actions, absolutely required in the current prior art, however, entail disadvantages. With sample carriers allowing for numerous detection reactions in a small space, as happens for instance with micro-titre or nano-titre plates, there exists the problem of "transfer," i.e. sample activity is transferred by washing from one sample volume to another one. A further disadvantage of the processes in which physical separation of unbonded and bonded label (or activity) occurs, consists of the fact that no time-staggered observation of the bonding process and hence no examination of the interaction or reaction kinetics is possible.

Besides the above cited washing for separation of bonded and unbonded activity, with assays using filter strips, separation takes place between unbonded activity and bonded activity by means of diffusion of the liquid phase in the porous solid phase formed by the filter. Assays of this type are usually set up for single samples.

SUMMARY OF THE INVENTION

The present invention is based on the technical problem of indicating a method for quantitative or qualitative determination of an analyte or its reaction or interaction kinetics which no longer shows the disadvantages of the present prior art, in particular one which avoids the washing steps required under the prior art.

A further problem consists in indicating a method of the type cited above by which sample volumes of <1 $\mu$l in micro-array arrangement can be analysed.

A further problem consists also in indicating agents which are suitable for conducting the method constituting the invention.

The technical problem cited above is solved in this invention by a method for quantitative or qualitative determination of an analyte or its interaction or reaction kinetics in a system with at least two different phases, comprising the step of taking at least one measurement signal from at least one of the phases, in which context the different phases when taking the measurement signal are present in parallel and each measurement signal is attributed to one of at least two phases.

The method cited constituting the invention allows for said determinations of an analyte without physical separation between unbonded and bonded label taking place prior to taking at least one such measurement signal.

The method is suitable for qualitative detection of the presence of an analyte in a sample. Furthermore, through temporarily successive taking of measurement signals when a binding equilibrium set in or with the unfolding of chemical reactions, the different process kinetics can be established. However, the method preferably serves for quantitative determination of an analyte in an analysis sample.

A common process scenario can be described as follows: After administration of the sample to be analysed, for instance into the well of a nano-titre plate which, by way of example, is coated with a specific bonding partner for the analyte, in the case of a competitive assay, a defined quantity of the labelled analyte is added. After the binding equilibrium sets in, at least one measurement signal is taken from a volume segment of the liquid phase, in which case the signal generated by the solid phase is essentially not taken. The measurement signal taken from the one phase, in the case of our example: the liquid phase, then serves for calculation of the quantity of analyte contained in that phase and ultimately for determination of the quantities of the analyte present in the sample under study. The quantitative evaluation of the measurement signal obtained occurs with a previously created calibration curve in which, under measurement conditions which remain constant, the strength of the signal of submitted and defined analyte concentrations is calculated.

Even qualitative analysis is possible in this way. If, for instance, an analyte is detected in a so-called sandwich format, then for example, a second labelled antibody can only bond to the first unlabelled antibody in the solid phase if an analyte is present. Detection of a signal in the solid phase thus means that an analyte must be present in the sample.

Kinetics can ultimately be calculated in this way in which, for instance, taking of the measurement signal in the liquid phase can be pursued via a temporal sequence. Modification of the signal in the liquid phase over time is the measure of the kinetics of a reaction or interaction of the analyte under study.

Measurement of a specific quantitative unit of one of the phases can in this way be ensured through corresponding adjustment of the measurement device. Thus, for instance, a laser beam which can be used to stimulate fluorescent-labelled molecules in the analysis sample, can be so arranged that only a certain quantitative segment of a phase, e.g. the liquid phase, is hit by the laser beam and only the molecules in the trajectory of the beam are excited into fluorescence. The fluorescent signal obtained in this way can then serve for calculation of the analyte concentration present.

In a particularly preferred embodiment, the method is carried out as an affinity assay. In doing so, the specific interaction between analyte and one bonding partner is exploited. Examples for an analyte and an associated bonding partner are a ligand as an analyte and a receptor as an associated bonding partner, nucleic acid as an analyte and complementary nucleic acid as a bonding partner, substratum as analyte and associated enzyme as a bonding partner, antigen as analyte and antibody as the corresponding bonding partner. A detailed survey of common processes of affinity analysis is found in C P Price & D J Newman (editors), "Principles and Practice of Immunoassay", Stockton Press, New York, 1991.

In an additional preferred embodiment, the method is carried out as an immuno-affinity assay. In this kind of assay, for detection of the analyte the specific interaction between antigen and antibody is exploited. As antibody for the specific detection of the analyte, so-called monoclonal as well as polyclonal antibodies can be used. Even the analyte serving as antigen can in turn constitute an antibody.

In a further preferred embodiment, the volume in which the detection reaction occurs, amounts to 1 $\mu$l or less, the volume preferably being some 50–100 nl. The volume of the detection reaction corresponds to the sample volume deployed including the reagents added. The prior art knows no process in which such small sample volumes can be subjected to one of the determinations cited above, particularly not if the samples are in a micro-array as when in a nano-titre plate.

With a further preferred embodiment the method is carried out as a competitive assay. In doing so, the analyte to be detected competes with a structurally similar compound which normally carries a label, for a limited number of bonding positions. Since the added and labeled substance competing with the analyte is administered in constant quantities, the number of bonding positions occupies by the structurally similar labeled substance depends on the number of bonding positions taken up by the analyte in the analyte concentration. This means that the more analyte that is present in the sample, the fewer the bonding positions which are occupied by the labeled competitive substance. This in turn means, that with increasing analyte concentration, the quantity of unbonded, labeled competitor in the liquid phase increases. This results in the measurement signal from the liquid phase increasing with an increase in the volume of analyte in the sample. Competitive assays are long since known to the person skilled in the art from the prior art.

However, the method can alternatively be carried out as a sandwich assay. In doing so, for instance, the analyte to be determined is implemented with two different antibodies. Here, a first antibody is bound to the solid phase, and the second antibody bears a label and is administered to the analysis sample. When interaction is completed, a ternary complex is formed in the solid phase consisting of the first antibody, the analyte and the labelled second antibody. In doing so, the signal in the solid phase increases with increasing analyte concentration while the concentration of the labelled second antibody in the liquid phase decreases with increasing analyte concentration. If a volume element of the liquid phase is measured in detection, then decreasing signal strength is observed with increasing analyte concentration. The sandwich assay principle is well known to the person skilled in the art from the prior art.

The measurement signal is preferably obtained by a label which is present as a component of the analyte or of the bonding partner (reactant). Suitable labelling possibilities are known to the person skilled in the art from the prior art. They include radioactive label, label produced by irradiation excitement such as labelling done, for instance, by fluorescent markers, or labelling with an enzyme activity. As a particularly preferred label, a fluorescent group is introduced into the molecule in question. Here fluorescence can be generated for example by having the labelled molecules excited by a laser beam. This technique is also well known to the person skilled in the art from the prior art.

In a further preferred embodiment, the system with which the process is carried out comprises a first phase constituting a solid phase and a second phase constituting a liquid phase. Here the solid phase generally bears the specific bonding partner for the analyte to be detected while the liquid phase is formed by the sample containing the analyte and the detection reagents. In a further alternative, the second phase can, however, also be a gaseous phase while the first phase constitutes the solid phase. Finally, the combination of phases can also consist of the combination of a liquid phase with a gaseous phase.

In a further preferred embodiment, the solid phase is formed by the walling of a well in a solid sample carrier. In doing so, the solid sample carrier can be fashioned so that it is only suited to absorbing a single sample. But the sample carrier can also be formed so that several samples can be absorbed simultaneously.

In a particularly preferred embodiment, the solid sample carrier is a micro-titre plate of the type commercially available. Particularly preferred is a nano-titre plate being used as a sample carrier, since the former has a large number of wells for absorbing the sample in a small space. The wells in the solid sample carrier can have different shapes. These include the quadratic or cylindric shape, truncated pyramid or truncated cone. Particularly preferred are, additionally, shapes whose aperture surface is smaller than their bottom surface; these include by way of example the negative truncated pyramid and the negative truncated cone. With this embodiment, mitigation of the measurement results from stray light/fluorescence on the part of label bound to the solid carrier is minimised by comparison with the corresponding embodiments whose bottom surface is smaller than their opening surface (such as with a positive truncated pyramid or positive truncated cone).

In a further preferred embodiment, the influence of interference effects from the label bound to the phase is lowered by having the phase contain a quenching substance. This quenching substance absorbs the signal generated by the molecules arranged in immediate proximity to the quenching substance. Preferably, the quenching substance is selected so that it quenches the fluorescence obtained when the molecules present in the system are excited by a laser. Preferably, the material quenches the fluorescence within a short distance, preferably less than 100 nm. As preferred materials, metals such as gold or silver, as well as graphite or dyes with "quenching properties" can be considered.

By way of example, the solid phase can contain such a quenching substance. For this purpose, the sample carrier can be coated with quenching material. This is particularly advantageous in cases where only the fluorescence of molecules located in the solution is to be recorded.

Receiving the measurement signal from only one of the signal generating phases present can, for instance, be obtained by space-staggered measurement. This can be done by having a laser beam sense the entire well in which the sample is located and, depending on its resolution capacity, several measurement signals can be obtained. The individual measurement signals represent the intensity of fluorescence occurring at each position and can thus be used for determination of the local concentration of an analyte.

Basically, however, it suffices if only a single measurement signal corresponding, for instance, to a defined volume element of the liquid phase, is taken.

In addition to this, by taking several signals of a phase, for instance by sensing the sample with a laser beam, the statistics can be improved by averaging out such measurement signals and thus the determination of an analyte or the interaction or reaction kinetics can be improved as well as errors in determining an analyte or interaction or reaction kinetics can be reduced.

In accordance with a further preferred embodiment, the quenching substance can be provided so that radiation of one phase is almost completely suppressed. According to this embodiment, it is not necessary to carry out spatially staggered taking of at least one measurement signal for attribution to the corresponding phase. If, for example, the walling and/or the floor of the well of a sample carrier is coated with quenching material, then the fluorescence resulting from the label bound to the walling can be suppressed and the fluorescence stemming from label in the liquid phase can be taken without requiring staggering of space. In one preferred embodiment, a spot with a diameter of 40 $\mu$m or less, preferably of about 20 $\mu$m, is illuminated and the generated signal of this volume segment is measured only.

Illuminating the sample volume segment is preferably done with a laser where the generated signal is a fluorescence which is emitted by the fluorophore-bearing molecules excited by the laser.

According to the invention, a sample carrier is also made available having one or more wells and which is characterised by the fact that at least a part of the sample carrier is at least in the range of one or more wells coated with fluorescence-quenching material.

This sample carrier can in particular be used in the processes described above for suppressing the fluorescent radiation of one phase. Of course, the applications of such a sample carrier are not limited to the processes described above; rather, such a sample carrier can also be used in other processes in which, for example, reducing stray radiation requires that fluorescence be quenched in a specific range.

According to an advantageous embodiment, the fluorescence-quenching material can comprise a metal such as, by way of example, gold or silver. If needed, this metal can also be doped.

The well or wells can advantageously be coated with the fluorescence-quenching material in accordance with the requirements in the floor area and/or the walling.

In addition, the advantages already described in connection with the processes can be achieved by different shapes of wells. Thus wells can be provided for in the sample carriers which have a quadratic, cylindrical, truncated pyramid or truncated cone shape. As likewise described above, it is particularly advantageous to provide a well whose aperture surface is smaller than its bottom surface. These include, in particular, a negative truncated pyramid shape or a negative truncated cone shape.

According to a further advantageous embodiment, the sample carrier is shaped in the form of a micro-titre plate, preferably a nano-titre plate. In this way, it becomes possible to analyse a number of samples with an optimum expenditure of time.

BRIEF DESCRIPTION OF THE DRAWINGS

Here below, preferred embodiments of the invention and examples of the method constituting the invention are described with reference to the enclosed drawing. The following is shown in the drawing.

DETAILED DESCRIPTION OF THE PREFERRED EMBODIMENT

Figure 1:
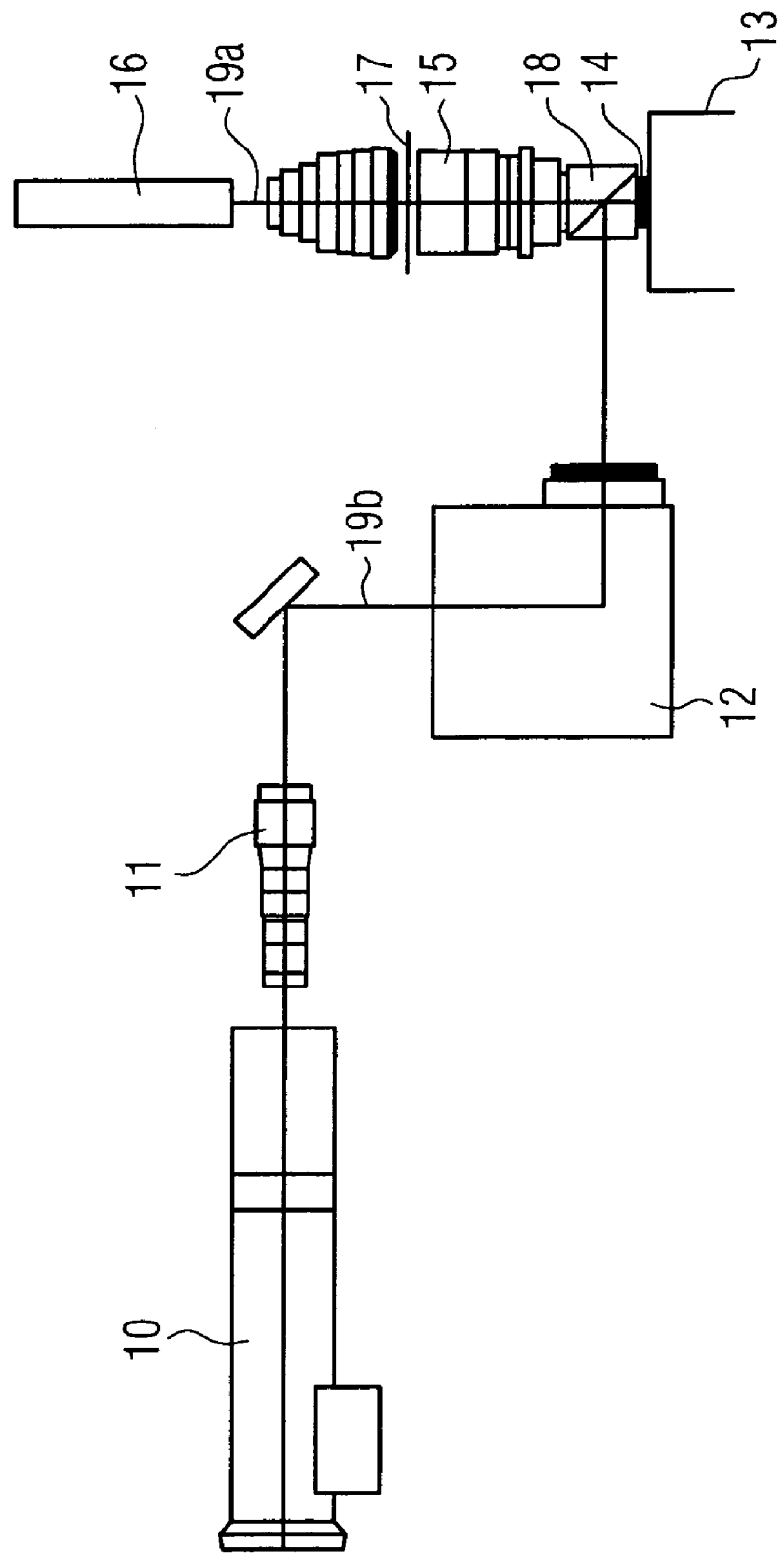
FIG. 1 A schematic view of an arrangement for carrying out the method constituting the invention.

1. Components for Carrying Out the Process a) Sample Carrier

For example, a planar sample carrier having one or more wells, which can absorb a liquid volume of 1 $\mu l$ or less, can be used. Its surface is covered with material which massively reduces (quenches) fluorescence at a short distance (below 100 nm). The quenching material is preferably a metal, gold and/or silver; however, it can also be graphite or a dye with quenching properties. The sample carrier's surface is further covered with a bonding partner for the analyte. The bonding partner can be an antigen or an antibody. The bonding partner can either be fixed through adsorption or through covalent bonding to the sample carrier. Suitable coating procedures are known to the person skilled in the art.

b) Reagents

An essential component is constituted by a fluorescence-labelled bonding partner specific to an analyte (e.g. an antibody), which can specifically bond to the analyte. Basically, the bonding partner is in a position to bond to free analytes in the sample as well as to an immobilised analyte on the sample carrier. Processes for manufacturing fluorescence-labelled antibodies are known to the person skilled in the art.

As further reagents, substances can be used which can prevent or reduce non-specific bonding of solid components, i.e. analyte or bonding partners, to the sample carrier. For this purpose, for instance, proteins or detergents can be considered. Substances suitable for suppressing non-specific bonds to the sample carrier are known to the person skilled in the art.

c) Selection Device

A lense device is used allowing stimulation of the fluorescence-labelled molecules present in the wells and allowing for detection of the fluorescent light emitted. Here the fluorescence can be excited and/or detected spatially-staggered inside any well. In this way, selective measurement of the fluorophores present in the solution is possible without separation of bound and free fluorophores being necessary. Selective measurement can be done by means of various variations of the measurement device. It is possible to so condition the stimulation lense so that only fluorophores in solution are excited while fluorophores in solid phase are not excited. Alternatively, it is possible by varying the detection lense to only record such fluorescence as is emitted by molecules in solution while fluorescence emitted by solid-phase bound molecules is not recorded. Finally, it is possible by varying the sample carrier accordingly to only record fluorescence stemming basically from molecules found in solution. This is made possible by wells for absorbing the sample which show a negative truncated pyramid in cross-section. Naturally, a combination of the alternatives cited can also achieve the desired effect.

2. Quantitative Determination With the Aid of a Competitive Assay

For quantitative determination of a dissolved analyte in a liquid sample, the following steps are carried out:

A sample carrier is prepared in which one or more wells are coated with a test system component, e.g. an antibody. This coating can be separated temporally and spatially from the carrying out of the actual quantitative determination. Additionally, the sample carrier can be modified in different ways in different wells.

The sample and the reagents required are introduced into one or more wells. Where needed, the well can then be sealed with a suitable agent for further storage.

The sample is incubated with the reagents until the binding equilibrium between analyte and bonding partner has set in.

The fluorescence of the molecules present in the sample is excited or detected under conditions under which either essentially the molecules in solution are excited or the molecules bound to the surface are excited. Possible is also sequential stimulation of the fluorescence molecules distributed among both phases, perhaps by grid-shaped sensing of the sample carrier.

In the competitive assay described, the fluorescence signal in the sample solution rises with the analyte concentration while the fluorescence signal on the walling of the sample carrier decreases with increasing analyte concentration. Decreasing of the fluorescence signal with increasing analyte concentrations is reinforced if the surface of the sample carrier is coated with a fluorescence quenching substance. The signal obtained can in the usual manner be calibrated with reference measurements and correlated with the concentration of the analyte.

3. Measuring Device for Carrying Out the Process

FIG. 1 shows schematically a possible measurement arrangement. Such a measurement arrangement is known, for instance, from Dixon's U.S. Pat. No. 5,381,224. This measurement arrangement consists of a laser 10, a mass-produced available beam expander 11, a sensing device or scanner 12, a specially designed test table 13 for securing a sample carrier 14, an imaging lense 15 as well as a detection device for detecting fluorescent radiation 16, and, for example, one or more photo-multipliers. In addition, the system can have a suitable filter combination 17. Fluorescence stimulation by means of the laser 10 occurs in this case via the beam expander 11, the scanner 13 and a beam splitter 18, for example in the form of a dichroitic mirror, on the sample. The fluorescence radiation 19a emitted by the sample is, in the reflected direction, captured by the beam splitter 18 with an imaging lense 15 recessed into the detection device 16. From the position of the laser beam 19b, known from controlled regulation of the scanner 13, every light signal can be attributed unambiguously to a point on the sample carrier 14 and thus to a sample to be measured or to sample volumes. The intensity of the signal obtained in the detection device 16 serves as a quantitative measure for analyte concentration in the sample.

4. Configuration of the Sample Carrier

The sample carrier used possesses at least one well but will generally comprise more than one well. Here both micro-titre as well as nano-titre plates can be used as sample carriers.

Figure 2:
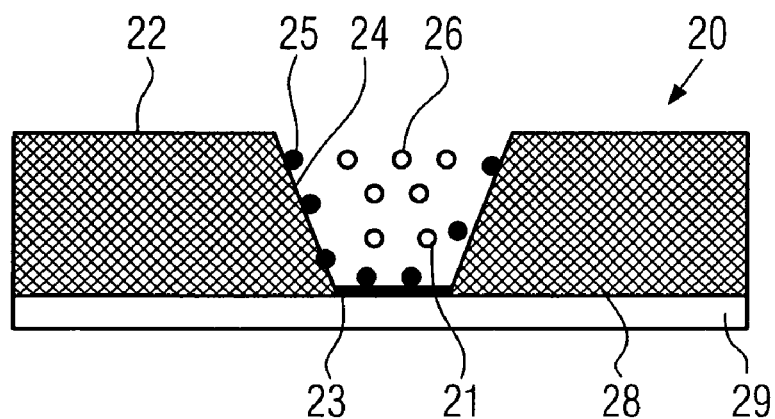
FIG. 2 A well of a sample carrier according to an embodiment of the present invention.

In FIG. 2, a partial view of a micro-titre plate 20 is depicted which has a truncated pyramid shaped well 21. The micro-titre plate 20 is covered with a fluorescence-quenching coating 22, for example of gold and/or silver. The coating of the sample carriers with gold as a quenching substance can be carried out with a vacuum metallising unit (Edwards 305) by means of thermal vaporisation of the gold. The sample carriers are first cleaned with laboratory cleaners (Extran, Merk), dried and then introduced into the metallising chamber. At a vacuum of better than $10^{-6}$ bar, coating thicknesses of 500 nm to 1000 nm of gold have been shown to be useful.

According to FIG. 2, the entire surface of the micro-titre plate is coated. This entails simplification in manufacturing the coating. Complete coating of the micro-titre plate is, however, not required. Rather, depending on the specific conditions emerging from a particular analysis, only the floor 23 and/or the walling 24 of the well can also be coated. The sample carrier shown in FIG. 2 is produced by having a silicium substratum 28 pickled by means of the shape of the well by means of different wet-pickling techniques such as anisotropic wet-pickling and the silicium substratum is subsequently provided with a floor 29.

In FIG. 2, there are further fluorophores 25 bound to the walling and the floor and fluorophores 26 in solution are depicted.

Figure 3:
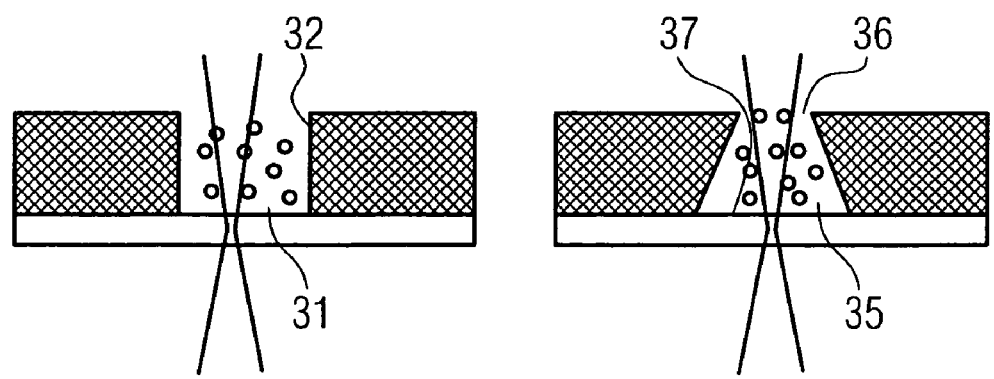
FIG. 3 Various shapes of wells of a sample carrier according to different embodiments of the present invention.

Of major importance for the quality of the measurement signal obtained is the fashioning of the well. Due to the spatially restricted stimulation with a focussed laser light source, primarily molecules in solution are detected. For reducing the fluorescence stimulation of the molecules bound to the solid phase, vertical walling 32 can be used in the wells 31 as they are shown in the left illustration of FIG. 3. Such vertical walling is found in a quadratically or cylindrically shaped well.

For almost complete elimination of fluorescence stimulation of the molecules bound to the walling, special well shapes are suitable whose aperture surface 36 is smaller than their floor surface 37. In the right illustration of FIG. 3, for instance, a cross-section of such a well 35 is depicted. This well 35 has a truncated pyramid or truncated cone shape. These varying shapes result in no direct fluorescence stimulation of the molecules bound to the walling taking place and furthermore with no detection of residual fluorescence, initiated by stray light in the aqueous phase, occurring.

Consequently, with wells of this shape, fluorescence is practically exclusively measured on molecules in the aqueous phase.

5. Quantitative Determination of a Pesticide

In the experiment, a pesticide derivative from the category of substituted S-triazines was determined. As bonding partner for such an analyte, antibodies were used.

Polyclonal sheep antibodies were enriched from serum by means of fractionated ammonium sulphate precipitation and isolated via an affinity column (Sephadex column, containing the immunogen).

Monoclonal antibodies were isolated from hybridom culture residues (serum-free culture) and cleaned via a protein G column.

For fluorescence labelling, a commercially available reactive fluorescent dye (CY5-N-hydroxy-succinimide, Amersham-Pharmacia-Biotech) was used. Labelling of the antibodies was done according to the manufacturer's instructions. The labelled antibodies were cleaned by means of spin dialysis (Amicon Concentrators, Aminco). The labelling degree is determined spectro-photometrically.

Conjugates of beef serum albumin (BSA) and haptene were produced as follows: From a triazine carboxyl derivative (atrazine caproic acid), an active ester was produced in DMF with di-isopropyl carbodimide (Sigma) and N-hydroxy-succinimide (Sigma). 1 mg of BSA in 100 mM of carbonate buffer, pH 9.0 was compounded with an excess of active esters and incubated for one hour at room temperature. The Conjugate was cleaned by means of spin dialysis (Amicon Concentrator, Aminco). The labelling degrees were determined spectro-photometrically.

Coating of the sample carriers with gold as quenching substance was done in a vacuum metallising unit (Edwards 305) by means of thermal vaporisation of gold. The sample carriers were cleaned with laboratory cleaner (Extran, Merk), dried and introduced into the metallising chamber. At a vacuum of better than $10^{-6}$, 500 nm to 1000 nm of gold were metallised. For comparative purposes, in each case a portion of the sample carrier was covered over during the metallisation process. After metallisation, the gold coatings were pickled in ethanol for one day in a solution of 0.2% -mercaptopropionic acid, washed with ethanol and dried.

The surfaces of the sample carriers, e.g. the micro-titre plates (Greiner Labortechnik) or the nano-titre plates (Ge-SIM, volume of the cup 600 $\mu$m×600 $\mu$m at a depth of 400 $\mu$m, equivalent to about 50 nl volume, truncated pyramid shaped wells, anisotropically pickled in silicium), were covered with the conjugate as follows: The surface was incubated for one hour with a solution of the conjugate in phosphate-buffered brine, pH 7.4. Subsequently, the surface was washed and incubated for an additional hour with a solution of 1 mg/ml BSA in order to saturate off non-specific bonding positions. For stabilising the coating, for one hour it was incubated with a solution of 0.5% glutaranhydride (Sigma). Subsequently, the sample carriers were washed and either immediately used or dried and stored at 4° C. For comparative experiments, the surfaces were only coated with BSA but not with a BSA pesticide conjugate.

5.1 Quantitative Determination of an Atrazine Derivative as Haptene with Mechanical Separation of Bound and Free Antibodies In the experiment, the atrazine coated micro-titre plates described above were used. The experiment describes the quantitative determination of antibodies directed at atrazine, in which case the antibodies in the dissolved fraction were determined after separation from the solid phase.

Figure 4:
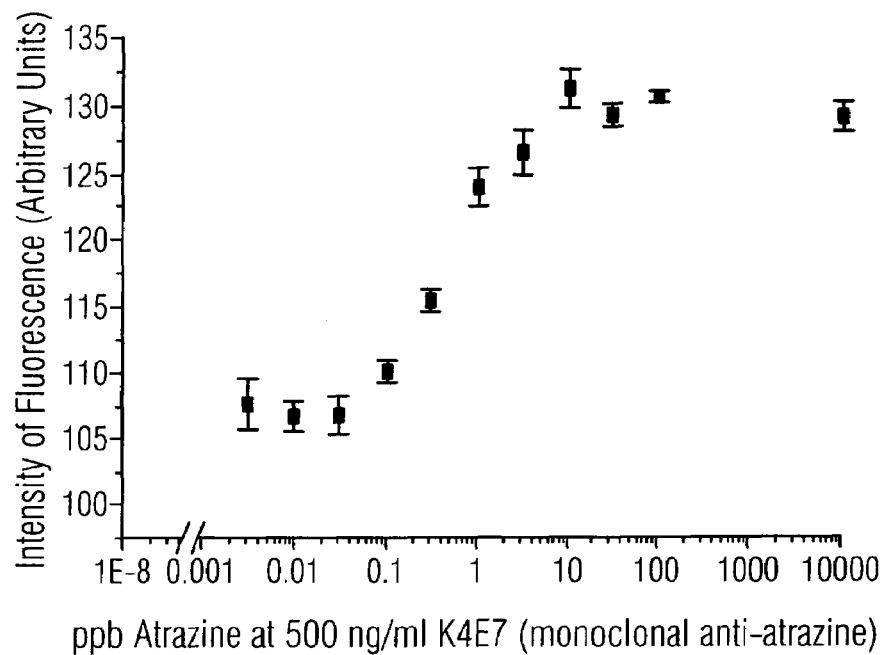
FIG. 4 A calibration graph showing fluorescence intensity as a function of the concentration of the analyte (atrazine) when using a monoclonal antibody according to a first example of the method constituting the invention.
Figure 5:
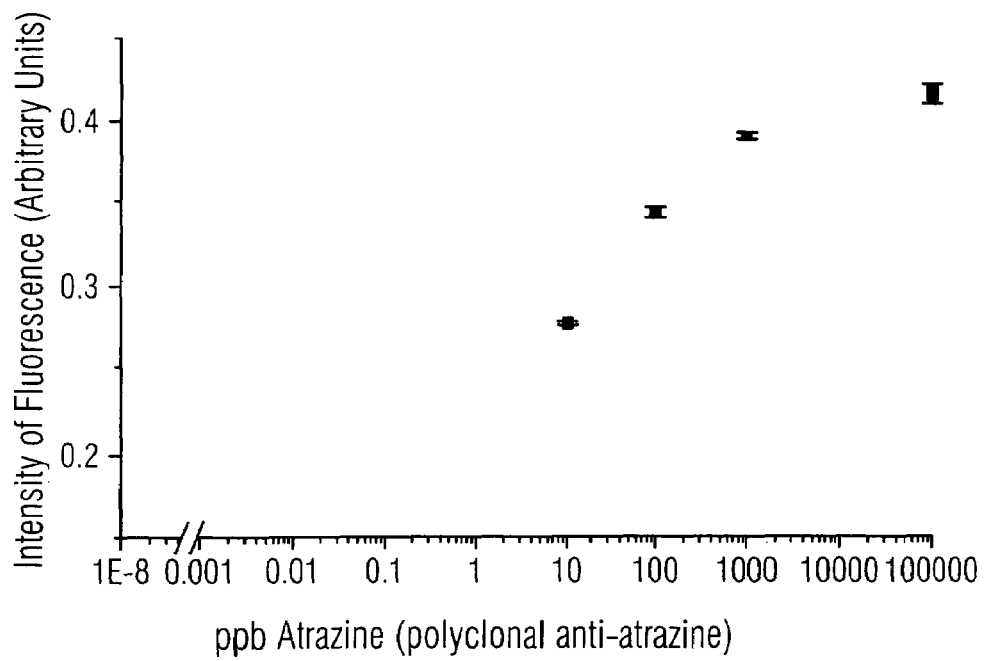
FIG. 5 A calibration graph showing fluorescence intensity as a function of the concentration of the analyte by using a polyclonal antibody according to a second example of the method constituting the invention.

Into each well of a micro-titre plate with an atrazine derivative, as described above, at first 100 µl of an atrazine solution was introduced, followed by 100 µl of a solution of fluorescence-labelled anti-atrazine antibodies. The final concentration of atrazine in the solution varied between 0.003 µg/l and 1000 µg/l. The antibody concentration amounted in each case to 500 ng/ml. After an incubation period of one hour at room temperature, from each well of the micro-titre plate 150 µl of solution was removed and introduced into the well of an opaque white fluorescence micro-titre plate (Perkin Elmer). Fluorescence was measured with a micro-titre plate fluorescence photometer (Perkin Elmer LSR 2000, stimulation at 670 nm, detection at 700 nm). FIG. 4 shows the calibration graph obtained for one monoclonal antibody; FIG. 5 shows the calibration graph for one polyclonal antibody. Fluorescence intensities are specified in arbitrary units. Both calibration graphs show a clear and significant link between intensity of fluorescence and the concentration of the analyte (atrazine).

Both in the case of using monoclonal antibodies as well as when using polyclonal antibodies, quantitative determination of the atrazine was possible in a concentration of less than 1 µg/l.

5.2 Determination of the Spatial Fluorescence Distribution on a Miniaturised Sample Carrier In this experiment, it is shown that settling of fluorescence-labelled bond molecules on the walling of the sample carrier entails spatial distribution of the fluorescent signal, such distribution deviating in a clear and measurable manner from spatial distribution without the settling of fluorescence-labelled bond molecules to the walling.

A GeSIM sample carrier was, as described above, treated and covered on one half with BSA only and on the other half with BSA atrazine conjugate. Into each well was introduced with a piezo-microdrop system (MICRODROP) 50 nl of a solution of fluorescence-labelled anti-atrazine antibodies in phosphate buffered brine (pH 7.4) with 100 µg/ml ovalbumin. The antibody concentrations were 0.2 µg/ml 0.5 1 µg/ml and 1.0 µg/ml. Subsequently, the plate was sealed with a transparent adhesive tape (Adhesive Research) and incubated for 30 minutes at room temperature. Subsequently, a spatial image of the intensity of fluorescence of the plate was produced with a laser scanner by sensing line-for-line the sample carrier (stimulation by means of the adhesive tape at 632 nm, detection with a photo-multiplier at 690 nm). In the structure used, a spot with a diameter of about 20 µm was illuminated by laser on the sample carrier. By means of a computer-assisted data recording system, an image of the fluorescence intensity distribution was sketched with spatial resolution of 50 µm in arbitrary units. For each well, an image of about 10×10 pixels resulted from this.

Figure 6:
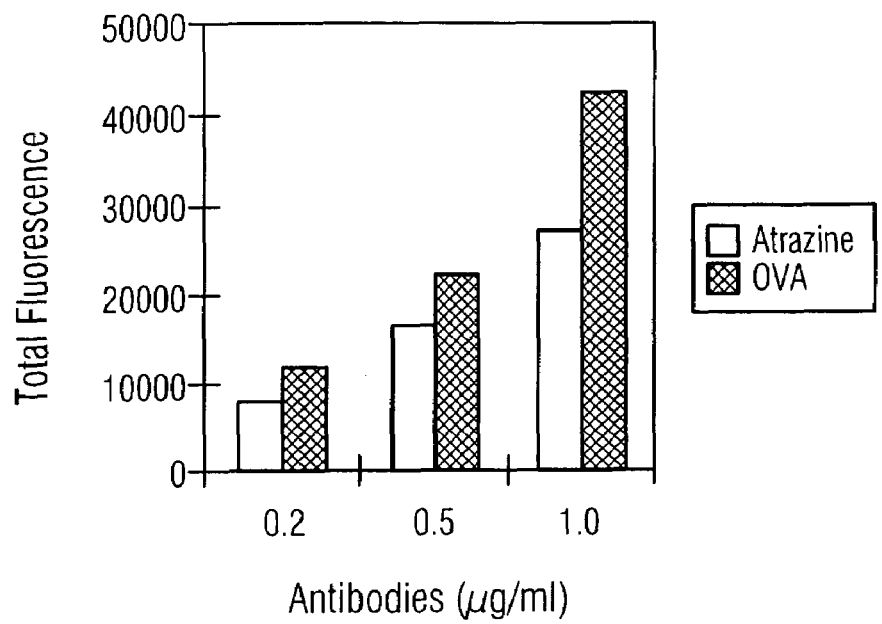
FIG. 6 A view for explaining the connection between the concentration of the analyte and the intensity of fluorescence.

For evaluation, the intensity of the fluorescence for each square well was determined by summation across all 100 attributed pixels. The result of this summation is depicted in FIG. 6. In FIG. 6, "atrazine" refers to the signals from the wells coated with an atrazine protein conjugate. "OVA" refers to the wells coated exclusively with ovalbumin. The total fluorescence for both, i.e. wells coated with atrazine protein conjugate as well as for those exclusively coated with ovalbumin, increases with antibody concentration.

In order to determine the spatial distribution of fluorescence, the mean intensity ($I_4$) per pixel for a square of 4×4 pixels in the middle of each well was determined, the mean intensity ($I_{10}$) being determined for the entire well (10×10 pixels). From these two readings, the quotient $I_4/I_{10}$ was determined. These results are depicted in FIG. 7.

Figure 7:
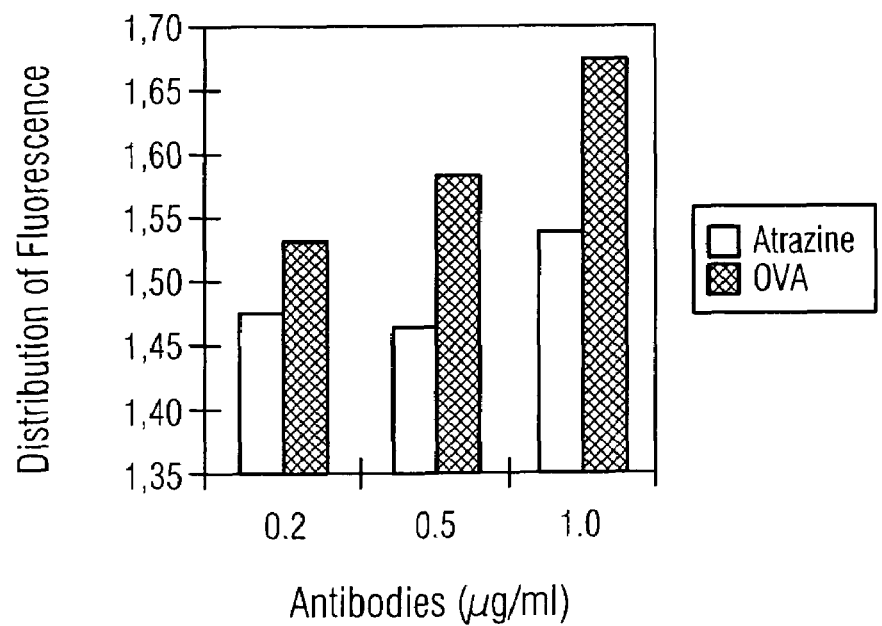
FIG. 7 A first view for explaining the determination of a spatial fluorescence distribution according to a further embodiment of the method constituting the invention.
Figure 8:
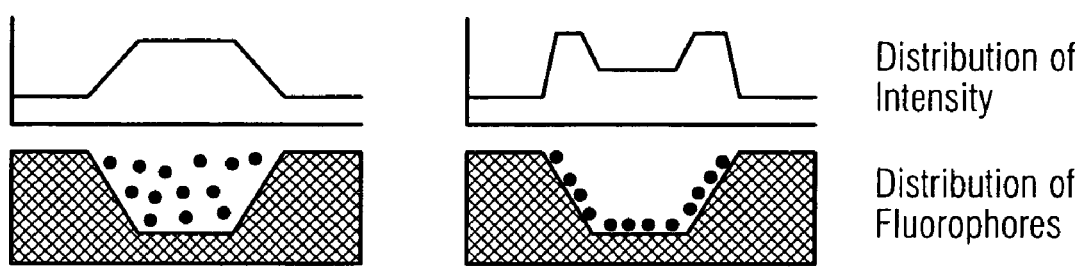
FIG. 8 A second depiction for explaining the determination of a spatial fluorescence distribution according to a further embodiment of the method constituting the invention.

In FIG. 7, "atrazine" again refers to the signals from the wells coated with an atrazine protein conjugate and "OVA" to wells coated exclusively with ovalbumin. For wells in which no bonding of the antibody to the walling occurs (OVA; see left illustration in FIG. 8), the mean fluorescence in comparison with the wells in which the antibody bonds to the walling (atrazine; see right illustration in FIG. 8) is increased, This effect is largely independent of the concentration.

To be noted in this context is that the laser beam is widened by the concave surface of the liquid meniscus upon entering the liquid sample. By means of this and by means of reflection in the well, the local selectivity of stimulation is limited. By means of the variation of the sample carrier indicated as constituting the invention, as well as of the stimulation and/or detection system, a significantly better signal profile can be achieved. For all concentrations of antibodies used, as expected, a decline in fluorescence asymmetry, i.e. a lesser emphasis of the mean of deeper bonding of the antibodies to the walling took place.

5.3 Quenching of the Fluorescence Signal with Settling of Fluorescence-Labelled Bonding Molecules to Walling of a Miniaturised Sample Carrier Coated with Fluorescence-Quenching Material The experiment serves to show that the settling of fluorescence-labelled bonding molecules to gold coated walling of the sample carrier entails significant decrease in the fluorescence signal, which decrease can be prevented by administering an analyte in liquid phase, something which makes the method suitable for quantitative determinations.

A GeSIM sample carrier was vaporised with gold, as described above, further treated and covered on one half with BSA only, and on the other half with BSA atrazine conjugate. Into each well was introduced with a piezo-microdrop system (MICRODROP) 50 nl of a solution of fluorescence-labelled anti-atrazine antibodies (1 µg/ml) in phosphate buffered brine (pH 7.4) with 100 µg/ml of ovalbumin. Into a portion of the wells there was additionally introduced an atrazine derivative with a concentration of 100 ng/ml. The following table provides the average readings for each of the 10 wells.

|  | Fluorescence (arbitrary units) | % error |
|---|---|---|
| 1 mg/ml ovalbumin/PBS (background) | 5149 | 1.7 |
| 1 µg/ml fluorescence-labelled antibody without atrazine derivative | 43574 | 1.8 |
| 1 µg/ml fluorescence-labelled antibody with 100 ng/ml of atrazine derivative | 65866 | 1.2 |

The fluorescence of the antibody decreases upon bonding to the walling by about 33% ("without atrazine derivative"). The correspondingly higher fluorescence upon adding of the atrazine derivative is explained by the blocking of the antibody bonding positions. In this way, the antibodies are not bound closer to the fluorescence-quenching walling of the sample carrier. When a sample carrier which has only been coated with BSA is used, no comparable effect was found. The reproducibility of the method is satisfactory and allows for quantification of modifications of fluorescence.

What is claimed is:

1. A method for quantitative or qualitative determination of an analyte comprising:
   (a) incubating a sample containing the analyte with a predetermined amount of labeled competitive substance and a solid phase coated with a quenching substance, wherein the solid phase further comprises an analyte-specific bonding partner immobilized thereto, such that the analyte and the labeled competitive substance compete for binding to the analyte-specific bonding partner, wherein the quenching substance suppresses signal from the labeled competitive substance bound to the solid phase;
   (b) exciting the sample so as to generate signal from unbound labeled competitive substance; and
   (c) measuring the signal only generated from the unbound labeled competitive substance in a volume segment of liquid phase, thereby quantitatively or qualitatively determining the analyte, wherein the determination of the analyte is performed or effected without physically separating the inbound and bound labeled competitive substance.

2. The method according to claim 1 in wherein the quenching substance is gold, silver or graphite.

3. The method according to claim 1, wherein the labeled competitive substance is selected from the group consisting of antigen, antibody, nucleic acid, ligand or receptor.

4. The method according to claim 3 in which the method is an immuno-affinity assay.

5. The method according to claim 1 in which the analyte comprises a nucleic acid.

6. The method according to claim 1 which the analyte determination is performed or effected in a volume of less than 1 $\mu$l.

7. The method according to claim 6 in which the volume is in the range of 50 to 100 nl.

8. The method according to claim 1 in which the labeled competitive substance is a fluorescent labeled reagent.

9. The method according to claim 1 in which the sample is in a liquid phase.

10. The method according to claim 1 in which the solid phase is formed on a wall of a well in a sample carrier.

11. The method according to claim 10 in which the carrier is a micro-titre or nano-titre plate.

12. The method according to claim 11 in which the sample carrier is a nano-titre plate.

13. The method according to claim 10 in which the well has a quadratic, cylindrical, truncated pyramid or truncated cone shape.

14. The method according to claim 10 in which the well has an aperture area and a floor area, the aperture area being smaller than the floor area.

15. The method according to claim 14 in which the well has a truncated pyramid or truncated cone shape.

16. The method according to claim 1 in which the measurement signal is obtained by spatially staggered measurement.

17. The method according to claim 1 in which a light beam is used to excite the sample, said light beam having a diameter of less than 40 $\mu$m.

18. The method according to claim 17 in which a laser provides the light beam.

19. The method according to claim 18 in which the light beam has a diameter of about 20 $\mu$m.

20. The method according to claim 1 in which the quenching substance is a metal, dye or fluorescence-quenching substance.

21. A method for qualitative determination of an analyte comprising:
   (a) incubating a sample containing the analyte with a labeled competitive substance, and a solid phase coated with a quenching substance, wherein the solid phase further comprises an analyte-specific bonding partner immobilized thereto, such that the analyte and the labeled competitive substance compete for binding to the analyte-specific bonding partner, wherein the quenching substance suppresses signal from the labeled competitive substance bound to the solid phase;
   (b) exciting the sample so as to generate signal from unbound labeled competitive substance; and
   (c) measuring the signal only generated from the unbound labeled competitive substance, thereby qualitatively determining the analyte, wherein the determination of the analyte is performed or effected without physically separating the unbound and bound labeled competitive substance.

22. The method according to claim 21, wherein the signal generated from the unbound labeled competitive substance is measured in a volume segment of liquid phase.

23. The method according to claim 22 in which the quenching substance is a metal, dye or fluorescence-quenching substance.

24. The method according to claim 21 in which the analyte comprises a nucleic acid.

25. The method according to claim 21, wherein the labeled competitive substance is selected from the group consisting of antigen, antibody, nucleic acid, ligand or receptor.

26. The method according to claim 25 in which the method is an immuno-affinity assay.

27. The method according to claim 21 in which the analyte determination is performed or effected in a volume of less than 1 $\mu$l.

28. The method according to claim 27 in which the volume is in the range of 50 to 100 nl.

29. The method according to claim 21 in which the labeled competitive substance is a fluorescent labeled reagent.

30. The method according to claim 21 in which the sample is in a liquid phase.

31. The method according to claim 21 in which the solid phase is formed on a wall of a well in a sample carrier.

32. The Method according to claim 31 in which the sample carrier is a micro-titre or nano-titre plate.

33. The method according to claim 32 in which the sample carrier is a nano-titre plate.

34. The method according to claim 31 in which the well has a quadratic, cylindrical, truncated pyramid or truncated cone shape.

35. The method according to claim 31 in which the well has an aperture area and a floor area, the aperture area being smaller than the floor area.

36. The method according to claim 35 in which the well has a truncated pyramid or truncated cone shape.

37. The method according to claim 21 in which the measurement signal is obtained by spatially staggered measurement.

38. The method according to claim 21 in which a light beam is used to excite the sample, said light beam having a diameter of less than 40 $\mu$m.

39. The method according to claim 38 in which a laser provides the light beam.

40. The method according to claim 39 in which the light beam has a diameter of about 20 $\mu$m.

41. The method according to claim 21, wherein the quenching substance is gold, silver or graphite.

* * * * *